(12) United States Patent
Scott

(10) Patent No.: US 11,052,040 B1
(45) Date of Patent: Jul. 6, 2021

(54) TOPICAL APPLICATION AND METHOD OF ADMINISTRATION AND ABSORPTION

(71) Applicant: Tirent Emanuel Scott, Spring Valley, CA (US)

(72) Inventor: Tirent Emanuel Scott, Spring Valley, CA (US)

( * ) Notice: Subject to any disclaimer, the term of this patent is extended or adjusted under 35 U.S.C. 154(b) by 363 days.

(21) Appl. No.: 15/998,324

(22) Filed: Mar. 23, 2019

(51) Int. Cl.
| | |
|---|---|
| *A61K 9/00* | (2006.01) |
| *A61K 33/34* | (2006.01) |
| *A61K 33/30* | (2006.01) |
| *A61K 33/32* | (2006.01) |
| *A61K 33/42* | (2006.01) |
| *A61K 33/44* | (2006.01) |
| *A61K 33/18* | (2006.01) |
| *A61K 33/04* | (2006.01) |
| *A61K 33/22* | (2006.01) |
| *A61K 47/46* | (2006.01) |
| *A61K 36/74* | (2006.01) |
| *A61K 47/44* | (2017.01) |
| *A61K 33/26* | (2006.01) |
| *A61K 31/197* | (2006.01) |
| *A61K 31/4188* | (2006.01) |
| *A61K 31/519* | (2006.01) |
| *A61K 33/06* | (2006.01) |
| *A61K 31/455* | (2006.01) |
| *A61K 33/24* | (2019.01) |
| *A61K 31/714* | (2006.01) |
| *A61K 31/4415* | (2006.01) |
| *A61K 31/51* | (2006.01) |
| *A61K 31/525* | (2006.01) |

(52) U.S. Cl.
CPC .......... *A61K 9/0014* (2013.01); *A61K 31/197* (2013.01); *A61K 31/4188* (2013.01); *A61K 31/455* (2013.01); *A61K 31/519* (2013.01); *A61K 33/04* (2013.01); *A61K 33/06* (2013.01); *A61K 33/18* (2013.01); *A61K 33/22* (2013.01); *A61K 33/24* (2013.01); *A61K 33/26* (2013.01); *A61K 33/30* (2013.01); *A61K 33/32* (2013.01); *A61K 33/34* (2013.01); *A61K 33/42* (2013.01); *A61K 33/44* (2013.01); *A61K 36/74* (2013.01); *A61K 47/44* (2013.01); *A61K 47/46* (2013.01); *A61K 31/4415* (2013.01); *A61K 31/51* (2013.01); *A61K 31/525* (2013.01); *A61K 31/714* (2013.01)

(58) Field of Classification Search
CPC ...... A61K 33/44; A61K 36/74; A61K 31/714; A61K 31/51; A61K 31/4415; A61K 31/525
See application file for complete search history.

(56) References Cited

U.S. PATENT DOCUMENTS 5,571,441 A * 11/1996 Andon ................... A61K 45/06
252/1

* cited by examiner

*Primary Examiner* — Kortney L. Klinkel

(57) ABSTRACT

The present invention relates to a composition for boosting immunity in a person comprising a plurality of minerals, a plurality of vitamins, activated charcoal, coffee beans, vitamin B complex and a carrier, wherein the carrier is an oil-based substance. The composition is an aggregation of the active agents/ingredients conventionally prepared. The present invention allows absorption of multiple active agents/ingredients in the body, consistently. The blend of vitamin and minerals get easily absorbed in the body of a patient without affecting the function of the liver.

10 Claims, No Drawings

TOPICAL APPLICATION AND METHOD OF
ADMINISTRATION AND ABSORPTION

BACKGROUND

Technical Field of Invention

The embodiments herein generally relate to a topical composition and more particularly to a composition comprising plurality of minerals and vitamins for improving an immunity in a patient.

DESCRIPTION OF RELATED ART

Vitamins and minerals are considered essential nutrients—because acting in concert, they perform hundreds of roles in the body. Vitamins help shore up bones, heal wounds, and bolster the immune system. Vitamins also convert food into energy, and repair cellular damage.

It has long been recognized that individuals living in poverty who suffer from malnutrition are more susceptible to infections and certain diseases due to deficiencies in macronutrients such as proteins, lipids, and carbohydrates. More recently, it has come to light that micronutrients such as several vitamins and minerals also play major roles in boosting the immune system to protect against certain infections, inflammation, and possibly some cancers. One major vitamins like A, B, C, D, and E have been reported to boost up the immune system by strengthening the activity of immune cells during any pathogen attack or in the case of the intrusion of some toxic materials either inhaled from air or that may be present in the foods. Vitamins A and D have received attention in recent years as these vitamins have been shown to have an unexpected and crucial effect on the immune response.

There have been supplements that helps in boosting the immunity of a person. These supplements mostly comprise an amalgamation of vitamins which must be taken orally. Sometimes, there are side-effects which leads to problems like nausea and vomiting.

Hence there is a need to develop a composition for boosting an immunity in a person that can be applied topically and which gets absorbed easily in the body. Also, there is a need to provide a composition which is a rich source of minerals as micronutrients.

The above-mentioned shortcomings, disadvantages and problems are addressed herein, as detailed below.

SUMMARY OF THE INVENTION

The primary object of the embodiments herein is to provide a composition for topical application for booking the immunity of a patient.

Another object of the embodiments herein is to provide a composition for topical application comprising a combination of plurality of vitamins and minerals.

Yet another object of the embodiments herein is to provide a composition for topical application that gets absorbed easily while the vitamins and minerals get safely absorbed into the body.

Yet another object of the embodiments herein is to provide a composition for topical application for boosting the immunity of a patient without burdening the liver.

Yet another object of the embodiments herein is to provide a composition that is applied topically on the soles of the feet and palms of the hands while the active ingredients gets easily absorbed in the body without affecting the function of liver.

According to an embodiment herein, a composition for boosting immunity in a person comprises a plurality of minerals, a plurality of vitamins, activated charcoal, coffee beans, vitamin B complex and a carrier, wherein the carrier is an oil-based substance.

According to an embodiment herein, the plurality of minerals are present in a quantity of 90% by weight.

According to an embodiment herein, the plurality of minerals comprises zinc, selenium, calcium, magnesium, potassium, copper, iron, sulphur, phosphorous, iodine, chromium, boron, chlorine, cobalt, silicon, germanium, sodium, manganese, vanadium, and molybdenum.

According to an embodiment herein, the plurality of vitamins are present in a quantity of 2% by weight.

According to an embodiment herein, the activated charcoal is present in a quantity of 2% by weight.

According to an embodiment herein, the coffee beans is present in a quantity of 2% by weight.

According to an embodiment herein, the vitamin B complex is present in a quantity of 2% by weight.

According to an embodiment herein, the carrier is present in a quantity of 2% by weight.

According to an embodiment herein, the carrier is selected from the group consisting of coconut oil, avocado oil, grapeseed oil, and olive oil.

According to an embodiment herein, the zinc is present in a quantity of 10 mg, selenium is present in a quantity of 10 mg, calcium is present in a quantity of 10 mg, magnesium is present in a quantity of 1 mg, potassium is present in a quantity of 1 mg, copper is present in a quantity of 1 mg, iron is present in a quantity of 1 mg, sulphur is present in a quantity of 1 mg, phosphorous is present in a quantity of 1 mg, iodine is present in a quantity of 1 mg, chromium is present in a quantity of 1 mg, boron is present in a quantity of 1 mg, chlorine is present in a quantity of 1 mg, cobalt is present in a quantity of 1 mg, silicon is present in a quantity of 1 mg, germanium is present in a quantity of 1 mg, sodium is present in a quantity of 1 mg, manganese is present in a quantity of 1 mg, vanadium is present in a quantity of 1 mg, and molybdenum is present in a quantity of 1 mg.

According to an embodiment herein, the composition is in the form of paste, liquid, spray, lotion, and powder.

According to an embodiment herein, the composition is applied topically under the soles of the feet or on the palms of the hands or anywhere topically on the skin.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide, a composition for boosting immunity in a person comprising a plurality of minerals, a plurality of vitamins, activated charcoal, coffee beans, vitamin B complex and a carrier, wherein the carrier is an oil-based substance.

According an embodiment herein, a composition for topical application is in the form of a paste, a liquid, a spray, a lotion, a powder and tablets having the properties of improving an immunity in a patient.

According an embodiment herein, a composition which is an aggregation of the active agents/ingredients conventionally prepared. The present invention allows absorption of multiple active agents/ingredients in the body, consistently.

According to an embodiment herein, a composition for boosting immunity in a person comprises a plurality of minerals, a plurality of vitamins, activated charcoal, coffee beans, vitamin B complex and a carrier, wherein the carrier is an oil-based substance.

According to an embodiment herein, the plurality of minerals are present in a quantity of 90% by weight.

According to an embodiment herein, the plurality of minerals comprises zinc, selenium, calcium, magnesium, potassium, copper, iron, sulphur, phosphorous, iodine, chromium, boron, chlorine, cobalt, silicon, germanium, sodium, manganese, vanadium, and molybdenum.

According to an embodiment herein, the plurality of vitamins are present in a quantity of 2% by weight.

According to an embodiment herein, the activated charcoal is present in a quantity of 2% by weight.

According to an embodiment herein, the coffee beans is present in a quantity of 2% by weight.

According to an embodiment herein, the vitamin B complex is present in a quantity of 2% by weight.

According to an embodiment herein, the carrier is present in a quantity of 2% by weight.

According to an embodiment herein, the carrier is selected from the group consisting of coconut oil, avocado oil, grapeseed oil, and olive oil.

According to an embodiment herein, the zinc is present in a quantity of 10 mg, selenium is present in a quantity of 10 mg, calcium is present in a quantity of 10 mg, magnesium is present in a quantity of 1 mg, potassium is present in a quantity of 1 mg, copper is present in a quantity of 1 mg, iron is present in a quantity of 1 mg, sulphur is present in a quantity of 1 mg, phosphorous is present in a quantity of 1 mg, iodine is present in a quantity of 1 mg, chromium is present in a quantity of 1 mg, boron is present in a quantity of 1 mg, chlorine is present in a quantity of 1 mg, cobalt is present in a quantity of 1 mg, silicon is present in a quantity of 1 mg, germanium is present in a quantity of 1 mg, sodium is present in a quantity of 1 mg, manganese is present in a quantity of 1 mg, vanadium is present in a quantity of 1 mg, and molybdenum is present in a quantity of 1 mg.

According to an embodiment herein, the composition is in the form of paste, liquid, spray, lotion, and powder.

According an embodiment herein, the present invention provides a composition for topical application and method for administration and absorption of active agents, wherein the absence of sebaceous glands in the palms of the hands and the sole of the feet allow for such absorption, said topical application can be formulated into a paste, liquid, spray, lotion, mud and tablets or to be applied onto or into patches, peel masks, socs, shoes, gloves and fabric. The active agents/ingredients comprise a plurality of vitamins and minerals.

According an embodiment herein, the present invention comprises a composition and method for administration and absorption of minerals into the body.

According to an embodiment herein, a composition for topical application and a method for administration is provided. The topical composition has an enhanced absorption characteristic. The composition allows the body to safely absorb the raw minerals into the body without burdening the liver wherein the body locate react to and absorb down to minute trace mineral located in food digested orally.

According to an embodiment herein, a composition for topical application comprises 90% minerals, 2% vitamins, 2% activated charcoal, 2% coffee beans, 2% vitamin B complex and 2% of coconut oil.

According to an embodiment herein, the carrier is infused with one or more variety of plants matter, sea weeds or plant derived extracts. These ingredients help in aiding the drying time after the composition is applied on the skin.

According to an embodiment herein, the composition is provided in the form of peel off patches. The composition comprises binders and natural fillers that help in cleanly peeling off the patch from the skin.

According to an embodiment herein, the see weeds are used as natural fillers.

According to an embodiment herein, the composition is provided in the form of insoles that is able to absorb all natural toxins from the body. The composition is in the form of disposable strips.

According to an embodiment herein, the minerals comprise or is selected from the group consisting of zinc, selenium, calcium, magnesium, potassium, copper, iron, sulphur, phosphorous, iodine, chromium, boron, chlorine, cobalt, silicon, germanium, sodium, manganese, vanadium, molybdenum.

Table 1 shows the quantity of each mineral present in the composition, according to an embodiment herein.

TABLE 1

| Quantity of minerals | |
| --- | --- |
| Mineral | Amount |
| Zinc | 10 mg |
| Selenium | 10 mg |
| Calcium | 10 mg |
| Magnesium | 1 mg |
| Potassium | 1 mg |
| Copper | 1 mg |
| Iron | 1 mg |
| Sulphur | 1 mg |
| Phosphorous | 1 mg |
| Iodine | 1 mg |
| Chromium | 1 mg |
| Boron | 1 mg |
| Chlorine | 1 mg |
| Cobalt | 1 mg |
| Silicon | 1 mg |
| Germanium | 1 mg |
| Sodium | 1 mg |
| Manganese | 1 mg |
| Vanadium | 1 mg |
| Molybdenum | 1 mg |

According to an embodiment herein, the composition further comprises vitamin B complex, wherein the vitamin B complex is present in a quantity of 5 mg. Vitamin B complex provide adrenalin for metabolism.

According to an embodiment herein, the composition further comprises activated charcoal, wherein the activated charcoal is present in a quantity of 0.1 mg.

According to an embodiment herein, the composition further comprises green coffee beans, wherein the green coffee beans is present in a quantity of 0.1 mg.

According to an embodiment herein, the composition further comprises a carrier, wherein the carrier is an oil-based substance. The carrier is selected from the group consisting of coconut oil, avocado oil, grapeseed oil, and olive oil. The oil is used as a carrier and to moisturize the skin. The oil further protects from unnecessary absorption of rubber or plastic from the insoles, laundry soaps, fabric softeners and other toxins temporarily.

Example 1

The topical composition of the present invention comprising a blend of vitamin and minerals dispersed in an oil-based carrier was used on patient. There was an improved immune system and excellent metabolism observed. Table 2 shows the statistics that were noted in the year 2016-year 2018.

| In year 2016 | In year 2018 |
|---|---|
| Blood pressure - 142/84 | Blood pressure - 96/66 |
| Body weight - 245 lbs | Body weight - 191 lbs |

Thus, the present invention relates to aggregation of the active agents conventionally prepared consistently, allowing bonding of multiple active ingredients thus allowing chemically said topical application to be place into the same vehicle for absorption included but not limited to cosmetic.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. A composition for boosting immunity, comprises:
a plurality of minerals;
a plurality of vitamins;
activated charcoal;
coffee beans;
vitamin B complex; and
a carrier, wherein the carrier is an oil-based substance.

2. The composition according to claim 1, wherein the plurality of minerals are present in a quantity of 90% by weight.

3. The composition according to claim 1, wherein the plurality of minerals comprises zinc, selenium, calcium, magnesium, potassium, copper, iron, sulphur, phosphorous, iodine, chromium, boron, chlorine, cobalt, silicon, germanium, sodium, manganese, vanadium, and molybdenum.

4. The composition according to claim 1, wherein the plurality of vitamins are present in a quantity of 2% by weight.

5. The composition according to claim 1, wherein the activated charcoal is present in a quantity of 2% by weight.

6. The composition according to claim 1, wherein the coffee beans is present in a quantity of 2% by weight.

7. The composition according to claim 1, wherein the vitamin B complex is present in a quantity of 2% by weight.

8. The composition according to claim 1, wherein the carrier is present in a quantity of 2% by weight.

9. The composition according to claim 1, wherein the carrier is selected from the group consisting of coconut oil, avocado oil, grapeseed oil, and olive oil.

10. The composition according to claim 1, wherein the zinc is present in a quantity of 10 mg;
selenium is present in a quantity of 10 mg;
calcium is present in a quantity of 10 mg;
magnesium is present in a quantity of 1 mg;
potassium is present in a quantity of 1 mg;
copper is present in a quantity of 1 mg;
iron is present in a quantity of 1 mg;
sulphur is present in a quantity of 1 mg;
phosphorous is present in a quantity of 1 mg;
iodine is present in a quantity of 1 mg;
chromium is present in a quantity of 1 mg;
boron is present in a quantity of 1 mg;
chlorine is present in a quantity of 1 mg;
cobalt is present in a quantity of 1 mg;
silicon is present in a quantity of 1 mg;
germanium is present in a quantity of 1 mg;
sodium is present in a quantity of 1 mg;
manganese is present in a quantity of 1 mg;
vanadium is present in a quantity of 1 mg; and
molybdenum is present in a quantity of 1 mg.

* * * * *